United States Patent [19]

Chaudhuri et al.

[11] Patent Number: 4,808,569

[45] Date of Patent: Feb. 28, 1989

[54] FRAGRANCE ADDITIVE

[75] Inventors: Ratan K. Chaudhuri, Butler; Michael W. Helioff, Westfield; Robert B. Login, Oakland, all of N.J.

[73] Assignee: GAF Corporation, Wayne, N.J.

[21] Appl. No.: 111,311

[22] Filed: Oct. 22, 1987

Related U.S. Application Data

[63] Continuation-in-part of Ser. No. 67,195, Jun. 29, 1987, and a continuation-in-part of Ser. No. 922,923, Oct. 24, 1986, Pat. No. 4,732,990.

[51] Int. Cl.$^4$ ................................................ A61K 7/46
[52] U.S. Cl. ................................................ 512/2; 512/3
[58] Field of Search ........................ 512/2, 3; 548/550

[56] References Cited

U.S. PATENT DOCUMENTS

| | | | |
|---|---|---|---|
| 3,250,784 | 5/1966 | Gensheimer et al. | 512/2 |
| 4,320,873 | 3/1982 | Martens et al. | 512/2 |
| 4,732,990 | 3/1988 | Login et al. | 548/550 |

*Primary Examiner*—James H. Reamer
*Attorney, Agent, or Firm*—Marilyn J. Maue; Joshua J. Ward

[57] ABSTRACT

The invention relates to a quaternized fragrance extender having the formula

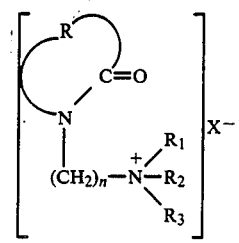

wherein n is an integer having a value of from 1 to 3; R is alkylene containing from 3 to 6 carbon atoms and is optionally substituted with lower alkyl; $R_1$ is alkyl containing from 8 to 22 carbon atoms; $R_2$ and $R_3$ are each independently alkyl containing from 1 to 22 carbon atoms and $X^-$ is an anion which quaternized compound is capable of complexing with volatile, odoriferous compounds of between 3 and 60 carbon atoms having an acidic hydrogen atom in its structure and to the complexed compound formed and the use of said complexed compound in perfume and other commercial products including cosmetics, cleaning agents, paints, soaps, deodorants, plastics and rubbers.

20 Claims, No Drawings

FRAGRANCE ADDITIVE

This application is a continuation-in-part of copending U.S. patent application, Ser. No. 067,195, filed June 29, 1987, entitled "QUATERNIZED NITROGEN CONTAINING COMPOUNDS" and of U.S. patent application, Ser. No. 922,923 filed Oct. 24, 1986, entitled "QUATERNIZED NITROGEN CONTAINING COMPOUNDS" now U.S. Pat. No. 4,732,990.

In one aspect, the invention relates to a novel fragrance additive and to the complexed compound formed by its addition as well as to the uses of such complexed products.

In another aspect, the invention relates to the synthesis of said complexed products.

BACKGROUND OF THE INVENTION

Fragrances for perfumery, cosmetics, detergents and in other commercial products are well known and have long been used to enhance, mask or heighten natural odors of various products or to provide a pleasing scent to the skin, hair or clothing. However, the scents and odors imparted by many of these fragrances are ephemeral, dissipating within a few hours. This is particularly true of aerosol sprays used for colognes, perfume and other cosmetic applications to the hair and skin where, because of the pressure and rapid evaporation of the propellant, many of the top notes and middle notes of the desired scent dissappear rapidly and the end note emerges without the complementary benefit of the top and middle components.

Also, fragrances added to commercial formulations, particularly those containing strongly acid or basic componets, tend to interact causing degradation of the scent desired, in some cases causing an unpleasant odor and discoloration.

Accordingly, it is an object of this invention to overcome the above deficiencies by means of an economical additive which can be produced by a commercially feasible and inexpensive process.

Another object is to prevent or minimize degradation of pleasing odors and to preserve the top and middle notes of a fragrance formulation.

Another object of this invention is to provide a fragrance component which is capable of masking unpleasant odors with a perfume formulation.

Another object is to heighten the natural odor of a substance.

Still another object is to lower the vapor pressure of a fragrance and extend its odoriferous emanation.

Yet another object is to stabilize fragrance compositions against chemical interaction in commercial formulations and to repress tendencies of discoloration.

THE INVENTION

In accordance with this invention there is supplied a lactone fragrance additive having the formula

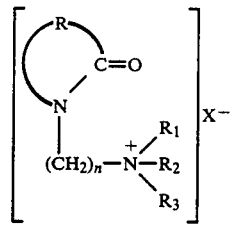

wherein n is an integer having a value of from 1 to 3; R is alkylene containing from 3 to 6 carbon atoms and is optionally substituted with lower alkyl; $R_1$ is alkyl containing from 8 to 22 carbon atoms; $R_2$ and $R_3$ are each independently alkyl containing from 1 to 22 carbon atoms and $X^-$ is an anion which additive reacts with fragances having an acidic hydrogen to form a complex through hydrogen bonding. Of the above lactams, those having a pyrrolidonyl or caprolactam ring system and wherein $X^-$ is a chloride anion and wherein at least one of $R_2$ and $R_3$ is lower alkyl, are preferred; although higher membered ring systems such as the 2-azacycloheptanone and 2-azacyclooctanone ring systems are also suitably employed. The heterocyclic rings of the present lactams can also be substituted with lower alkyl; hence trialkyl-[(3-methyl-2-pyrrolidonyl)methyl] ammonium salts, trialkyl-[(3-butyl-2-pyrrolidonyl)methyl] ammonium salts, trialkyl-[(3,4-diethyl-2-pyrrolidonyl)-methyl] ammonium salts, trialkyl-[(2,3-dimethyl-2-piperidonyl) propyl] ammonium salts, and the like are also included within the scope of this invention.

Examples of lactams suitably employed in the present invention include dimethyl[2-pyrrolidonyl)methyl] octadecyl ammonium salt methyl[(2-pyrrolidonyl)methyl] dioctadecyl ammonium salt propyl[(2-pyrrolidonyl)propyl] didecyl ammonium salt diethyl[(2-pyrrolidonyl)methyl] dodecyl ammonium salt dimethyl[(3-methyl-2-pyrrolidonyl)ethyl] heptadecyl ammonium salt dibutyl[(2-piperidonyl)methyl] dodecyl ammonium salt methyl ethyl [(4-ethyl-2-piperidonyl)ethyl] hexadecyl ammonium salt ethyl decyl[(2-azacycloheptanonyl)methyl] tetradecyl ammonium salt methyl[(2-azacyclonanonyl)ethyl] dioctyl ammonium salt butyl[(2-azacyclodecanonyl)methyl] dieicosyl ammonium salt dimethyl[(3,4-dimethyl-2-pyrrolidonyl)ethyl] 2,16-dimethyl-octadecyl ammonium salt diethyl[(3-butyl-2-pyrrolidonyl)methyl] 2,4,6-triethyl hexadecyl ammonium salt methyl[(2-pyrrolidonyl)methyl] didoeicosyl ammonium salt.

Of the above species, the chloride salts are preferred, although bromide, iodide and sulfate salts can also be employed, if desired. Most preferred of the above lactams are the pyrrolidonyl and piperidonyl ammonium chlorides.

The present quaternized lactams employed in this invention can be prepared by the process disclosed in co-pending U.S. patent application Ser. No. 067,195, filed June 29, 1987, entitled QUATERNIZED NITRO- GEN CONTAINING COMPOUNDS particularly on pages 7 through 13, which disclosure is incorporated herein by reference.

The fragrances or osmophores which form complexes with the above lactams are volatile, odoriferous compounds containing an acidic hydrogen which is joined to the lactam complex through hydrogen bonding with the carboxyl group. Fragrances of this type contain between 3 and 50 carbon atoms and include hydroxylated compounds, aldehydes, primary and secondary amines, primary and secondary amides, acids, and essential oils used for fragrances and perfumery. They may be synthetic or naturally occurring. The use of synthetically prepared fragrances with the present lactams enables the formulator to emphasize certain notes without interference by natural by-odors which the same fragrance would have were it isolated from the natural product. These synthetics are less expensive to obtain and possess more olfactory uniformity and stability than those made with essential oils, natural extractions and other organic materials which are subject to the vagaries of nature. Such synthetics include terpenes, aldehydes, jasmone, linalool and geraniol. However, natural products are used to provide more richness, subtility and natural character. Natural products include essential oils, spices, flower oils in the form of concretes, absolutes, extracts, etc. The hydroxylated compounds include both aliphatic and aromatic compounds which may be additionally substituted with alkyl, alkoxy, ether, ketone, aralkyl, alkaryl, aldehyde or vinyl groups or any combinations thereof. Among the essential oils of this type are included the oils from bergamot, cedarwood, citrus, geranium, guaiacwood, lemon, neroli, orange, patchoudi, rhondinal, rosemary, tangerine and ylang-ylang oils. Also included are extracts, gums and resins such as benzoin, galbanum, labdanum, maté, melilot, myrrh, frankincense, oakmoss, opopanax, orris, styrax and other balsam resins.

Sweet, herbal or floral fragrances are derived from $C_8$–$C_{11}$ aldehydes, amylcinnamic aldehyde, anesic aldehyde, benzaldehyde, hexylcinnamic aldehyde, methyl nonylacetalaldehyde, linalool, peach aldehyde, and oils from carnation, citrus, gardenia, heliotrope, hyacinth, honeysuckle, jasmin, jonquil, lavendar, lavandin, lilac, lilley-of-the-valley, mimosa, acacia, orange, rose, rose oxide, rosemary, violet, etc. Spicy fragrances are obtained from oils and extracts of bisal, bay, birch tar, caraway, cinnamon, cedar leaf, clove, clover, musk, nutmeg, oakmoss, orris root, sage, sweet grass, tuberose, tonka, vanillin, ethyl vanillin, benzyl alcohol, ambrettolide, galaxolide, geraniol, hexadecanolide, indole, albdanum, lemon grass, neroli, narcissus, petigrain resida, and ambergris fixative. Various alcohols, ethers and hydrocarbons which are satisfactory osmophores for this invention include phenyl ethyl alcohol, propanol, butanol, pentanol, dodecanol, ethyl sec-butyl ether, diethoxyethane, pinene, camphene, terpinene and others.

Of the above commercially employed fragrances, the hydroxylated compounds and aldehydes are most readily complexed with the present lactams and the most preferred compounds are those having the formula

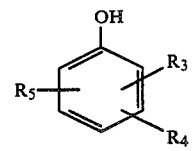

wherein $R_3$ is lower alkyl, lower alkoxy, phenyl or lower alkyl ester and $R_4$ and $R_5$ are each independently hydrogen, lower alkyl, lower alkoxy, lower alkenyl, aldehyde, phenyl or lower alkyl ester, Vanillin and ethyl vanillin are examples of this group.

The fragrances of this invention which complex with the present lactams are often employed as perfumery compositions. The following Tables 1–3 are representative examples of such compositions as used in perfumes, creams and soaps.

TABLE 1

Formulas for Rose Bases, parts by wt.

| Ingredients | Perfume | Cream | Soap |
|---|---|---|---|
| rhodinol | 50 | 15 | |
| geraniol coeur (perfume grade) | 5 | 15 | 15 |
| citronellol coeur | 10 | 30 | 15 |
| phenylethyl alcohol coeur | 10 | 15 | |
| phenylethyl alcohol white extra | | | 20 |
| nerol coeur | 5 | 5 | |
| geranyl acetate | 2 | 2 | 5 |
| aldehyde C-8, 10% | 4 | 4 | 5 |
| aldehyde C-9, 10% | 4 | 4 | 5 |
| benzophenone | 3.5 | 1.5 | 6 |
| rose oxide, 1% | 1 | 1 | |
| rosalva | 0.5 | 0.5 | 1 |
| geranium Bourbon, natural or artificial | | 5 | 15 |
| essence of styrax | 3 | 2 | 3 |
| guaiacwood oil | 2 | | 10 |

TABLE 2

Formulas for Jasmin Bases, parts by wt.

| Ingredients | Perfume | Cream | Soap |
|---|---|---|---|
| benzyl acetate | 20 | 20 | 30 |
| benzyl alcohol | 10 | 14 | 10 |
| linalyl acetate | 15 | 15 | 15 |
| linalool | 5 | 8 | 10 |
| jasmone or isojasmone | 1 | 1 | 1 |
| peach aldehyde C-14 (undecalactone), 25% | 1 | 1 | 1 |
| hexylcinnamic aldehyde | 8 | 10 | 10 |
| indole, 10% | 8 | | 1.5 |
| methyl anthranilate | 1 | | |
| ylang-ylang oil extra | 10 | 10 | |
| ylang-ylang oil artificial for soaps | | | 10 |
| phenylethyl alcohol coeur | 20 | 20 | |
| phenylethyl alcohol white extra | | | 10 |
| jasmine absolute | 1 | | |
| methyl β-naphthyl ketone | | 1 | 1.5 |

TABLE 3

Composition of a Floral, Woody, Oriental Perfume Concentrate, parts by wt.

| Ingredients | Perfume | Cream | Soap |
|---|---|---|---|
| base for perfume | 40 | | |
| base for creams | | 40 | |
| base for soaps | | | 40 |
| aldehyde C-10 (decyl aldehyde), 1% | 5 | 5 | 5 |
| aldehyde C-11 (undecylenic aldehyde), 1% | 3 | 3 | 3 |
| methylnonylacetaldehyde, 10% | 1 | 1 | 1 |
| oil of tangerine | 2 | | |
| oil of bergamot natural | 6 | | |

TABLE 3-continued

Composition of a Floral, Woody, Oriental Perfume Concentrate, parts by wt.

| Ingredients | Perfume | Cream | Soap |
|---|---|---|---|
| oil of bergamot artificial for soap | | | 6 |
| linalyl acetate | | 5 | |
| linalool | 2 | 3 | 2 |
| oil of neroli bigarade petals | 1 | | |
| oil of neroli artificial for creams and soaps | | 1 | 1 |
| dimethyl anthranilate, 10% | | 2 | 2 |
| oil of ylang-ylang extra | 5 | | |
| oil of ylang-ylang 2nd quality | | 5 | |
| oil of ylang-ylang for soaps | | | 5 |
| methylionone γ-coeur | 10 | | |
| methylionone γ-A | | 10 | 10 |
| synthetic rose | 12 | 12 | 12 |
| synthetic fasmin | 5 | 7 | 7 |
| oil of patchouli | 1 | 1 | 1 |
| tincture of natural musk (4 oz/gal) | 10 | | |
| tincture of civet (4 oz/gal) | 5 | | |
| Galaxolide (IFF), 50% | | 5 | 5 |
| jasmin absolute | 1 | | |
| rose absolute | 1 | | |

Perfumes are generally solutions of perfume concentrates or oils in alcohol. The strength of the solution of perfume oil in alcohol is about 10 to 25% or 12 to 32 oz per gal. The strength of the average successful perfume today is, in general, 15 to 20% or 18 to 24 ox per gal. For toilet waters and colognes the concentration of the fragrance component is much less, e.g. a typical formula for these products is about 3 grams of concentrate, 65 g. of 95% ethanol and 32 g. of dionized water.

All of the above described formulae are suitable for complexing with the present lactams and as complexes, have excellent hair and skin substantivity thus enabling them to be incorporated in many commercial formulations as exemplified in Table 4.

TABLE 4

Use Categories depilatories
special cleansers and detergents
permanent wave lotions
hormone creams and lotions
medicated creams and lotions
suntan lotions and oils
lotions
laundry rinses
creams
deodorants
hair rinses
miscellaneous hair treatment products
shampoos
makeup
face powders
lipsticks
colognes and perfumes
nail polish To form the fragrance complexes of the present invention, the osmophoric compound or fragrance formulation is mixed with the lactam in a weight ratio of between about 1:0.05 and about 1:10, preferably in a weight ratio of from about 1:0.2 to 1:6. The mixing is effected at a temperature at which the osmophoric component is liquid but non-volatile, e.g. a temperature within the range of between about 5° C. and 100° C. under from about 10 to about 50 psig., more often between about 20° C. and about 80° C. under atmospheric pressure. The mixing operation is continued until a homogeneous solution is obtained, generally within a period of between about 5 minutes and about 2 hours, preferably between about 15 and 30 minutes. The pH during the mixing operation is most desirably maintained at about 7; although a pH of from about 5.5 to about 8 is also practicable.

The above mixing operation can be carried out in the presence or in the absence of an inert liquid diluent, most desirably an inert liquid having a pleasing odor such as an alcohol or an ester, e.g. isopropyl myristate, isopropyl palmitate, etc., of which ethanol and ethyl acetate are particularly recommended. The concentration of such diluted solutions, when employed, can vary between about 0.1 and about 15%; although solutions of from about 0.5 to about 5% are conveniently employed.

The concentration of the complexed osmophoric component in a cosmetic or industrial formulation is usually less concentrated than in a perfume. For example, the complexed fragrance can represent between about 0.1 and about 25 wt. %, preferably between about 0.75 and about 15 wt. %, of such commercial formulations. Somewhat higher concentrations can be used in industrial products to mask unpleasant odors. When the complex is synthesized in the presence of a diluent the product solution can be employed directly for addition into a commercial product; on the other hand, when the complexed fragrance is prepared in the absence of diluent, the complexed product is generally diluted to a concentration within the above range for ease of mixing and uniform distribution in the cosmetic or detergent formulation.

For the purpose of the present invention, a detergent formulation is intended to include a shampoo, a liquid hard surface cleaner, a laundry detergent as well as a detergent rinsing solution.

Incorporation into a commercial formulation or cosmetic is carried out under the same conditions of mixing time, temperature and pressure as recited above for the formation of the complex. However, a buffer may be added to maintain the pH within a range of from about 5 to 8.5 during the blending operation. The present complexed fragrances are suitably employed as a component in any of the use categories outlined in Table 4, examples of which are as follows.

| | Vol. % |
|---|---|
| A. Standard Dishwashing Composition | |
| Water | 59.4 |
| Ethanol (95%) | 8.6 |
| Alfonic 1412-A 59.3% (ethylene oxide sulfate) | 20.0 |
| Alfonic 1412-10 (linear alcohol ethoxylate) | 1.1 |
| Sodium Chloride | .9 |
| Ethoxylated (9) nonyl-phenol (IGEPAL CA-630) | 7.5 |
| Fragrance | 2.5 |

| | % by Wt. |
|---|---|
| B. Machine Dishwashing Liquid | |
| Tetrasodium pyrophosphate | 22.00 |
| Sodium metasilicate | 10.00 |
| Sodium benzoate | 1.00 |
| Sodium xylene sulfonate (40%) | 1.00 |
| Glycol ether | 2.00 |
| Capryloamphocarboxy glycinate | 6.00 |
| 50/50 mixture of N—n-octyl- and N—n-dodecyl-2-pyrrolidones | 3.00 |
| Fragrance | 0.50 |
| H₂O | 54.50 |
| C. Fine Fabric Washing Detergent | |
| Linear decyl benzene sulfonate | 5.00 |
| Coconut diethanolamide | 20.00 |

-continued

| | |
|---|---|
| Sodium lauryl ether sulfate (3 mol EO) | 15.00 |
| Sodium xylene sulfonate (40%) | 10.00 |
| Citric Acid | to pH 7 |
| Preservative | Q.S. |
| Colorant | Q.S. |
| N—n-dodecyl-2-pyrrolidone | 5.00 |
| Fragrance | 2.50 |
| Water | to 100% |

D. Cold Water Phosphated Laundry Detergent

| | |
|---|---|
| Sodium tripolyphosphate | 48.0 |
| Sodium silicate (2:1 ratio) | 10.0 |
| Sodium sulfate | 17.5 |
| α-phosphono-w-(nonylphenoxy)-poly(oxy-1,2-ethanediyl) [GAFAC] | 17.5 |
| Fragrance | 2.0 |
| $H_2O$ | 5.0 |

E. Sanitizing Detergent

| | |
|---|---|
| Magnesium aluminium silicate | 0.90 |
| Kelzan gum thickener | 0.45 |
| tetrasodium EDTA | 1.00 |
| Monazoline-O*/Imidazoline | 1.00 |
| Hydrochloric acid (37%) | 20.00 |
| Barquat MB-80 (alkyl dimethyl benzyl ammonium chloride) | 1.25 |
| 50/50 mixture of N—n-octyl- and N—n-dodecyl-2-pyrrolidones | 3.00 |
| Fragrance | 1.00 |
| $H_2O$ | 71.40 |

*substituted imidazoline of oleic acid

| | % by Wt. |
|---|---|
| F. Leather, Vinyl and Other Plastic Liquid Cleaner | |
| Ethoxylated alkylphenol | 10.00 |
| Arcosolve PM (propylene glycol methyl ether) | 5.00 |
| Isopropyl alcohol | 2.50 |
| Amyl acetate | 1.00 |
| 50/50 mixture of N—n-octyl- and N—n-dodecyl-2-pyrrolidones | 2.00 |
| Fragrance | 12.00 |
| Preservative | Q.S. |
| $H_2O$ | to 100% |
| G. Liquid Rug Shampoo | |
| Sipex 7WC concentrate (blend of ionic and nonionic surfactants, $C_{12}$ av. chain length) | 10.00 |
| Lauryl ether sulfate (3 mole EO) | 10.00 |
| Sodium tripolyphosphate | 2.00 |
| Ethyl carbitol solvent | 1.50 |
| Tinopal 5BM optical brightener (diamino stilbene) | 0.05 |
| N—n-dodecyl-2-pyrrolidone | 2.00 |
| Fragrance | 8.00 |
| Preservative | Q.S. |
| $H_2O$ | to 100% |
| H. Spray-Wipe Furniture Polish | |
| Petrolite C-36 emulsion* (20%) | 3.50 |
| Isopar E solvent ($C_8$–$C_9$ isoparaffin mixture of branched chain aliphatic hydrocarbons) | 32.50 |
| S-Maz 80 (Sorbitan monooleate) | 0.20 |
| Masil EM 1000 emulsion (dimethyl polysiloxane silicone emulsion, 60% active) | 3.40 |
| 50/50 mixture of N—n-octyl- and N—n-dodecyl-2-pyrrolidones | 3.00 |
| Fragrance | 0.40 |
| $H_2O$ | 57.00 |

*reacted microcrystalline wax, m.p. 195° F., needle penetration at 77° F. is 7.5

| | % by Wt. |
|---|---|
| I. Toilet Bowl Cleaner | |
| Magnesium aluminum silicate | 0.90 |
| Xanthan gum thickener (Kelzan) | 0.45 |
| Tetrasodium EDTA | 1.00 |
| (Mona) Monazoline O Imidazoline | 1.00 |
| Hydrochloric acid (37%) | 20.00 |
| (Lonza) Barquat MB-80 | 1.25 |
| n-Octyl pyrrolidone | 1.50 |
| n-Dodecyl pyrrolidone | 1.50 |
| Fragrance | 20.00 |
| Water | Q.S. |

-continued

| | |
|---|---|
| | 100.00 |

J. Detergent Rinse Aid

| | |
|---|---|
| Nonoxynol 9 (9 av. ethoxylated nonyl phenol) | 30.00 |
| Isopropanol | 15.00 |
| Propylene glycol | 15.00 |
| N—n-octyl-2-pyrrolidone | 3.00 |
| Fragrance | 7.00 |
| $H_2O$ | 30.00 |

K. Fabric Softener

| | |
|---|---|
| Miranol DM (monocarboxylic stearic derivative, sodium salt) | 3.00 |
| Arquad 2HT 75 (dimethyl[hydrogenated tallow] ammonium chloride) | 2.00 |
| N—n-dodecyl-2-pyrrolidone | 1.00 |
| Fragrance | 0.25 |
| $H_2O$ | 93.75 |

L. Liquid Softening/Antistat Composition

| | |
|---|---|
| N—n-tetradecylpyrrolidone | 5.4 |
| (2) Igepal CO-660 | 23.0 |
| $H_2O$ | 55.7 |
| Ethanol | 15.0 |
| Fragrance | 0.9 |

(2) 100% active liquid/liquid condensation product of nonyl alcohol and ten units of ethylene oxide

| Ingredient | % by Wt. |
|---|---|
| M. SKIN LOTION | |
| Stearic Acid | 3.00 |
| Mineral Oil, 70 cts | 2.00 |
| Emulsifying Wax | 3.00 |
| Dimethicone | 1.50 |
| Deionized Water | QS |
| Carbomer 934* | 0.15 |
| Oleth-20** | 1.00 |
| N—decyl-2-pyrrolidone | 1.00 |
| Triethanolamine, 98% | 1.00 |
| Preservative | QS |
| Fragrance | 0.5 |
| N. FACIAL CREAM | |
| Mineral Oil, 70 cts | 6.00 |
| Petrolatum | 4.00 |
| Lanolin | 3.00 |
| Glyceryl Monostearate, S.E. Acid Stable | 19.00 |
| Glycerine | 1.00 |
| N—octyl-2-pyrrolidone | 2.00 |
| Deionized Water | QS |
| Preservative | QS |
| Fragrance | 0.1 |

*a crosslinked polymer of acrylic acid (B. F. Goodrich)
**the polyethylene glycol ether of oleyl alcohol (GAF Corp.)

| Ingredient | % by Wt. |
|---|---|
| O. SUNSCREEN LOTION | |
| Myristyl Myristrate | 1.00 |
| PVP/Eicosene Copolymer | 2.00 |
| Glyceryl Stearate, S.E. | 3.50 |
| Dimethicone | 1.00 |
| N—dodecyl-2-pyrrolidone | 2.00 |
| Deionized water | Q.S. |
| Carbomer 940 | 0.10 |
| Triethanolamine | 0.10 |
| Preservative (Germaben II)* | Q.S. |
| Octyldimethyl p-aminobenzoic acid | 4.00 |
| Fragrance | 0.80 |
| P. HAIR SHAMPOO | |
| $C_{14}$–$C_{16}$ Alpha Olefin Sulfonate | 20.00 |
| Ammonium Lauryl Sulfate | 25.00 |
| Cocamidopropyl Betaine | 3.50 |
| N—dodecyl-2-pyrrolidone | 1.00 |
| Sodium Laureth-4-Phosphate | 1.00 |
| Hydrolyzed Animal Protein | 0.25 |
| Tetrasodium ethylene diamine tetra acetic acid | 0.15 |
| Deionized water | Q.S. |
| Fragrance | 2.5 |
| Preservative (Kathon CG)** | Q.S. |

*N—[1,3-bis(hydroxymethyl)-2,5-dioxo-4-imidazolidinyl-N,N'-bis(hydroxymethyl)urea; Sutton Labs.
**5-chloro-2-methyl-4-isothiazolin-3-one (Rohm & Haas)

| Ingredient | % by Wt. |
|---|---|
| Q. BRUSHLESS SHAVING CREAM | |
| a. Stearic Acid | 20.00 |
| Cetyl Alcohol | 1.00 |
| Lanolin | 2.00 |
| Isopropyl Palmitate | 6.00 |
| (Part a. added molten and mixed with Part b. at 80° C.) | |
| b. Hexylene Glycol | 8.00 |
| Triethanol Amine | 1.80 |
| Potassium Hydroxide | 0.50 |
| Borax | 2.00 |
| N—tetradecyl-2-pyrrolidone | 2.00 |
| Deionized water | Q.S. |
| Preservative (Kathon CG) | Q.S |
| Fragrance | 3.00 |
| R. AEROSOL SHAVING CREAM | |
| Deionized Water | Q.S. |
| Glycerine | 5.8 |
| Oleth-20 | 1.0 |
| Butylated hydroxy anisole | 0.1 |
| Butylated hydroxy toluene | 0.1 |
| Stearic Acid | 7.5 |
| Lanolin | 0.5 |
| Mineral Oil, 70 cts | 2.4 |
| Cetyl Alcohol | 0.5 |
| Triethanolamine, 98% | 3.9 |
| Cocamide Diethanolamine | 0.5 |
| N—dodecyl-2-pyrrolidone | 2.0 |
| Fragrance | 0.5 |
| Concentrate:Propellant Ratio - 95:5 | |
| Propellant: A-46 [80:20 - Isobutane/Propane] | |

| | Parts by Wt. |
|---|---|
| S. Hand Lotion | |
| Water | 80 |
| Propylene glycol | 2 |
| Petrolatum | 3 |
| Srearic acid | 6 |
| Triethanolamine | 1 |
| Glycerin | 2 |
| N—dodecyl-2-pyrrolidone | 5 |
| Fragrance | 1 |

| | % by Wt. |
|---|---|
| T. Waterless Hand Cleaner | |
| Deionized Kerosene | 44.00 |
| Stearic acid | 4.00 |
| Ethoxylated nonyl phenol | 4.00 |
| Propylene glycol | 4.00 |
| Arcosolve DPM (dipropylene glycol monomethyl ether) | 3.00 |
| Triethanolamine | 1.00 |
| N—n-octyl-2-pyrrolidone | 3.00 |
| Fragrance | 2.00 |
| Preservative | Q.S. |
| H$_2$O | Up to 100% |
| U. Rug Shampoo | |
| Sodium lauryl sulfate | 12.00 |
| N—dodecyl-2-pyrrolidone | 3.00 |
| Sodium xylene sulfonate | 2.00 |
| Fragrance | 18.00 |
| H$_2$O | 100% |

Having generally described the invention, reference is now had to the following examples which provide preferred embodiments illustrating the invention but which are not to be construed as limiting to the scope thereof as more broadly defined above and in the appended claims.

EXAMPLE 1

Into a round bottom glass flask was introduced a 1:1 molar mixture of dimethyl-[(2-pyrrolidonyl)methyl] octadecyl ammonium chloride and vanillin and the mixture heated to 80° C. with agitation until a homogeneous liquid was obtained (about 30 minutes). The melt was then allowed to cool to room temperature and the product was collected in quantitative yield as a viscous liquid.

EXAMPLE 2

Example 1 was repeated except that methyl-[(2-pyrrolidonyl)methyl]]dioctadecyl ammonium chloride was employed as the complexing agent and the following composition was substituted as the fragrance component instead of vanillin.

| Osmophoric composition | WT. % |
|---|---|
| lilac extract | 8 |
| muguet | 5 |
| 3% musk extract | 5 |
| jasmine essence | 9 |
| tuberose absolute | 3 |
| 90% ethanol | 70 |

The pyrrolidonyl compound complexed with components of the jasmine essence, e.g. hexylcinnamic aldehyde and aldehyde C-14 to provide lasting fragrance.

EXAMPLE 3

The product of Example 1 (1.0 g) was dissolved in ethanol at room temperature to provide a 1% alcoholic solution. About 5 g. of the complex in solution was then mixed at room temperature into a conditioning shampoo having the following formulation:

| INGREDIENT | % BY WEIGHT |
|---|---|
| Deionized water | 48.65 |
| Sodium lauryl sulfate | 40.00 |
| Cocamide DEA | 2.50 |
| Cocamido propyl betaine | 3.50 |
| Sodium laureth 4-phosphate | 0.80 |
| Tetrasodium EDTA | 0.20 |
| Hydrolized silk protein | 0.25 |
| Stearyl pirrolidonium chloride | 4.00 |
| Methyl chloroisothiazolinone and methyl isothiazolinone | 0.10 |
| | 100.00 |

The complexed fragrance was mixed in the formulation at room temperature for about 5 minutes and then bottled for future use.

The above procedure was repeated except that, instead of the complex, 0.05 g. of vanillin in ethanol was added to the identified shampoo formulation.

After 14 days, the above formulations were used as a shampoo on two test subjects. The hair of both subjects was set and dried under similar conditions.

The formulation containing the complex retained the fragrance 24 hours longer than that which contained non-complexed vanillin fragrance. This extension of scent emanation was due to the skin and hair substantivity of the complexed form of the fragrance.

EXAMPLE 4

The product of Example 1 was dissolved in ethanol at room temperature to provide a 5% solution in alcohol. About 2.5 g. of the complex in solution was then added and mixed at room temperature into a standard roll-on antiperspirant having the following formulation.

| Ingredients | % by Wt. |
| --- | --- |
| deionized water | 50.00 |
| glyceryl monostearate (self emulsifying-acid stable) | 4.00 |
| isopropyl palmitate | 6.50 |
| ceteareth-55 (polyethylene glycol ether of cetearyl alcohol) | 1.00 |
| chlorhydrol (antiperspirant 50% soln.) | 38.50 |
| | 100.00 |

After a uniform mixture was obtained the solution was packaged in a roll-on dispenser. The above procedure then was repeated to provide 5 separate samples of antiperspirant containing the complex in roll-on dispensers.

The entire procedure described above was repeated, except that 2.5 g of non-complexed vanillin was substituted for the product of Example 1.

Ten volunteer female subjects were tested with the above samples, 5 with the antiperspirant containing the 1:1 complexed fragrance and 5 with the uncomplexed fragrance. It was found that the fragrance persisted for 18 hours with no noticeable perspiration odor on the subjects tested with the formulation containing the complexed fragrance; whereas, after 4 hours the fragrance had dispersed and a faint perspiration odor was detected after 5 hours on the subjected tested with the non-complexed fragrance formulation.

EXAMPLE 5

The above procedure in Example 4 is repeated except that an antiperspirant stick formulation having the following composition is substituted for the roll-on solution.

| Ingredient | % by Weight |
| --- | --- |
| aluminum zirconium tetrachlorohydrex GL 4 (REZAL 36GP) | 20.50 |
| Stearyl alcohol | 22.00 |
| Glyceryl monostearate (acid stable/self emulsifying) | 1.00 |
| Talc, 325 mesh | 1.00 |
| Carbowax 1000 (polyethylene glycol) | 5.00 |
| Cab-O-Sil-M-5-Silica* | 1.50 |
| Siloxane F-22 | 49.00 |
| | 100.00° |

*Fumed Silica

In the present case the complexed and non-complexed fragrances were incorporated by melting the above formulation, mixing in the osmophoric component until a uniform distribution was obtained, allowing the resulting composition to cool to room temperature and then recovering the product as a soft waxy substance. Ten male subjects were tested by rubbing on the soft stick antiperspirant. The fragrance emission on the five subjects tested with the composition containing the complexed fragrance stick deodorant lasted for 12 hours without any trace of perspiration odor. On the five subjects tested with the non-complexed fragrance stick deodorant the vanillin scent lasted only 4 hours, after which there was a noticeable odor of perspiration.

EXAMPLE 6

The product of Example 1 was dissolved in ethanol at room temperature to provide a 1% solution in alcohol. About 4 g. of the complex in solution was then added and mixed at room temperature into a standard pet shampoo having the following formulation.

| Ingredient | % By Weight |
| --- | --- |
| magnesium aluminum silicate (veegum, reg.) | 1.00 |
| deionized water | 41.30 |
| sodium cocoyl isethionate, 83% | 19.00 |
| sodium methyl cocoyl taurate, 24% | 26.00 |
| cetyl alcohol | 1.80 |
| glyceryl monostearate, acid stable | 5.90 |
| laneth - 10 acetate (polyethylene glycol ether of lanolin alcohol) | 3.50 |
| synergized pyrethrins (50% piperonyl butoxide and 10% pyrethrins) | 0.50 |
| captan (vancide 89 RE) | 1.00 |
| | 100.00 |

Five portions of pet shampoo were prepared as above and tested on 5 canines. After drying, the fur of the animals had a soft, silky appearance and, after 2 days the pleasing vanillin scent still adhered to the fur.

After 1 month, the above experiment was repeated except that 4 g. of non-complexed vanillin was added to the above pet shampoo formulation. The same canines were shampoo with the non-complexed fragrance composition. After drying, the fur, while soft, had noticeably less luster and the pleasing vanillin scent on the fur endured for only 12 hours. The improved results achieved with the present complexed fragrance is due to the high skin and hair substantivity of the complex and to the complexed form of the fragrance.

EXAMPLE 7

A. Into a round bottom glass flask was introduced a 5:1 molar mixture of dimethyl-[(2-pyrrolidonyl)methyl] dodecyl ammonium chloride and vanillin and the mixture heated to 80° C. with agitation until a homogeneous liquid was obtained (about 30 minutes). The melt was then allowed to cool to room temperature and the product was collected in quantitative yield as a viscous liquid. This product was diluted to a 5% solution with 24 parts 9 moles ethoxylated nonyl phenol, 15 parts ethanol, 55 parts water and 1 part cationic surfactant.

Ten cotton terry cloth towels were mechanically washed for 10 minutes with concentrated ALL (0.20% use level) detergent and then subject to a first rinse cycle for 2 minutes. The towels were drained to dampness by a 1 minute centrifuge cycle and then subjected to a second rinse at 45° C. At the beginning of the second rinse, 6.2 g. of the complexed vanillin, prepared as above was added to the rinse water to provide a rinse containing 0.03% of the complex. The towels were agitated in the second rinse for 3 minutes after which they were drained to dampness as above and dried in a mechanical dryer.

B. The entire procedure above was repeated except that 1 g. of non-complexed vanillin was similarly diluted and added to the second rinse water instead of the complexed vanillin.

The dried towels recovered from part A. were soft and pliable and retained the pleasing scent of vanillin for 4 days; whereas those recovered from part B. were somewhat stiffer and retained the vanillin scent for only 12 hours.

It will be understood that any of the afore-designated quaternary lactams can be substituted in the examples for complexing with the indicated fragrances or fragrance compositions and that any of the described fragrances or fragrance compositions can also be substituted in the examples to provide complexes with said quaternary lactams and to provide products having improved skin and hair substantivity and extended scent emanation. Also any of the formulations A-U can be substituted in the examples for incorporation of the complexed fragrances of this invention to provide improved formulations.

What is claimed is:

1. The complex of a quaternary lactam having the formula:

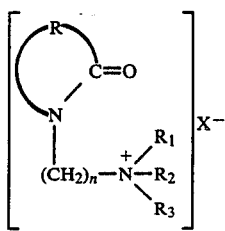

wherein n is an integer having a value of from 1 to 3; R is alkylene containing from 3 to 6 carbon atoms and is optionally substituted with lower alkyl; $R_1$ is alkyl containing from 8 to 22 carbon atoms; $R_2$ and $R_3$ are each independently alkyl containing from 1 to 22 carbon atoms and $X^-$ is an anion, with a volatile, odoriferous fragrance containing a compound having an acidic hydrogen atom and from 3 to 50 carbon atoms wherein the weight ratio of fragrance to quaternary lactam is between about 1:0.05 and about 1:10.

2. The complex of claim 1 wherein said compound is selected from the group consisting of a hydroxylated compound, an aldehyde, a primary or secondary amine, a primary or secondary amide, a carboxylic compound, an essential perfume oil and mixtures thereof.

3. The complex of claim 1 wherein said compound is a hydroxylated compound.

4. The complex of claim 3 wherein said hydroxylated compound is vanillin.

5. The complex of claim 1 wherein said anion is a chloride, bromide or iodide anion.

6. The complex of claim 5 wherein $R_2$ and $R_3$ are each independently lower alkyl and $R_1$ is alkyl having from 8 to 22 carbon atoms.

7. The complex of claim 1 wherein $R_1$ is octadecyl, $R_2$ and $R_3$ are lower alkyl, $X^-$ is a chloride anion and said compound is vanillin.

8. The complex of claim 7 wherein $R_2$ and $R_3$ are both methyl.

9. The complex of claim 5 wherein $R_1$ is alkyl having from 8 to 22 carbon atoms, $R_2$ is lower alkyl, $R_3$ is the same as $R_1$ or $R_2$, $X^-$ is a chloride anion and said compound is vanillin.

10. The complex of claim 9 wherein $R_1$ and $R_3$ are each octadecyl and $R_2$ is lower alkyl.

11. The complex of claim 10 wherein $R_2$ is methyl.

12. The process which comprises intimately mixing a volatile, odoriferous fragrance component containing a compound having an acidic hydrogen atom and from 3 to 50 carbon atoms and the quaternary lactam component of claim 1 in a weight ratio of between about 1:0.05 and about 1:10 at a temperature and pressure at which said components are in the liquid state to produce the complexed product of claim 1.

13. The process of claim 12 wherein said weight ratio is between about 1:0.2 and about 1:6.

14. The process of claim 12 wherein said compound is a hydrogenated compound.

15. The process of claim 14 wherein said compound is vanillin.

16. The process of claim 14 wherein at least one of $R_1$, $R_2$ and $R_3$ in said quaternary lactam component is octadecyl, another of $R_1$, $R_2$ and $R_3$ is methyl and $X^-$ is a chloride anion.

17. The process of adding an effective fragrance producing amount of the complex of claim 1 to a non-fragrant formulation.

18. The process of adding between about 0.1 and about 25 wt. % of the complex of claim 1 to a cosmetic formulation.

19. The process of adding between about 0.1 and about 25 wt. % of the complex of claim 1 to ethanol.

20. The process of adding between about 0.1 and about 25 wt. % of the complex of claim 1 to a detergent formulation.

* * * * *